(12) United States Patent
Armitstead

(10) Patent No.: US 8,066,647 B2
(45) Date of Patent: Nov. 29, 2011

(54) METHOD FOR DETECTING AND DISCRIMINATING BREATHING PATTERNS FROM RESPIRATORY SIGNALS

(75) Inventor: Jeffrey Armitstead, Bella Vista (AU)

(73) Assignee: Resmed Limited, New South Wales (AU)

( * ) Notice: Subject to any disclaimer, the term of this patent is extended or adjusted under 35 U.S.C. 154(b) by 1219 days.

(21) Appl. No.: 11/576,210

(22) PCT Filed: Dec. 21, 2005

(86) PCT No.: PCT/AU2005/001942
§ 371 (c)(1),
(2), (4) Date: Mar. 28, 2007

(87) PCT Pub. No.: WO2006/066337
PCT Pub. Date: Jun. 29, 2006

(65) Prior Publication Data
US 2008/0177195 A1    Jul. 24, 2008

Related U.S. Application Data

(60) Provisional application No. 60/638,169, filed on Dec. 23, 2004.

(51) Int. Cl.
*A61B 5/08*    (2006.01)

(52) U.S. Cl. ....................... 600/529; 600/538

(58) Field of Classification Search .............. 600/481, 600/483, 484, 529–543
See application file for complete search history.

(56) References Cited

U.S. PATENT DOCUMENTS

| | | | |
|---|---|---|---|
| 4,365,636 A | | 12/1982 | Barker |
| 5,203,343 A | * | 4/1993 | Axe et al. ........................ 600/538 |
| 5,794,623 A | * | 8/1998 | Forbes ........................... 600/515 |
| 5,947,908 A | * | 9/1999 | Morris ........................... 600/484 |
| 6,138,675 A | * | 10/2000 | Berthon-Jones ......... 128/204.23 |

(Continued)

FOREIGN PATENT DOCUMENTS

EP    1295623    3/2003

(Continued)

OTHER PUBLICATIONS

Leite, Joao, Alfredo Mansur, Humberto de Freitas, Paulo Chizola, Edimar Bocchi, Mario Terra-Filho, J. Alberto Neder, Geraldo Lorenzi-Filho, Periodic Breathing During Incremental Exercise Predicts Mortality in Patients with Chronic Heart Failure Evaluated for Cardiac Transplantation, 2003, Journal of the American College of Cardiology, vol. 41, 2175.*

(Continued)

*Primary Examiner* — Miranda Le
*Assistant Examiner* — Michael R Bloch
(74) *Attorney, Agent, or Firm* — Gottlieb Rackman & Reisman, PC

(57) ABSTRACT

A signal representative of a patient's respiration is split into equal length epochs. A primary feature is extracted from each epoch that acts as a compressed representation of the signal events. Statistics are applied to the primary feature to produce one or more secondary features that represent the entire epoch. Each secondary feature is grouped with one or more other features that are extracted from the entire epoch rather than selected epoch events. This grouping is the epoch pattern. The pattern is manipulated with suitable classifier algorithm to produce a probability for each class within the algorithm, that the signal may be representative of a disease state (Cheyne-Stokes, OSA etc). The epoch is assigned to the class with the highest probability. Also defined are methods of detecting Cheyne-Stokes breathing by analyzing a signal to detect one or regions of hyperpnoea and if the length of a hyperpnoea exceeds a parameter, Cheyne-Stokes is present.

4 Claims, 12 Drawing Sheets

U.S. PATENT DOCUMENTS

| | | | |
|---|---|---|---|
| 6,171,258 B1 * | 1/2001 | Karakasoglu et al. | 600/529 |
| 6,290,654 B1 * | 9/2001 | Karakasoglu | 600/529 |
| 6,811,538 B2 * | 11/2004 | Westbrook et al. | 600/529 |
| 7,381,185 B2 * | 6/2008 | Zhirnov et al. | 600/300 |
| 2002/0002327 A1 * | 1/2002 | Grant et al. | 600/324 |
| 2003/0187638 A1 * | 10/2003 | Causevic et al. | 704/226 |
| 2003/0199945 A1 | 10/2003 | Ciulla | |
| 2003/0233048 A1 * | 12/2003 | Silverman et al. | 600/500 |
| 2004/0071337 A1 * | 4/2004 | Jeung et al. | 382/151 |
| 2004/0254482 A1 * | 12/2004 | Anderson et al. | 600/484 |
| 2005/0256420 A1 | 11/2005 | Norman et al. | |
| 2005/0267362 A1 | 12/2005 | Mietus et al. | |
| 2006/0258921 A1 * | 11/2006 | Addison et al. | 600/323 |

FOREIGN PATENT DOCUMENTS

| | | |
|---|---|---|
| WO | 00/19895 | 4/2000 |
| WO | 00/20047 | 4/2000 |
| WO | 01/76459 | 10/2001 |
| WO | 02/26283 | 4/2002 |
| WO | 03/057025 | 7/2003 |
| WO | 2004/047618 | 6/2004 |
| WO | 2004/062485 | 7/2004 |
| WO | 2005/112760 | 12/2005 |

OTHER PUBLICATIONS

Extended Search Report, European Patent Office, Application No. 10150057.7, Feb. 26, 2010.
Daniel I. Loube et al (1999). "Comparison of Respiratory Polysomnographic Parameters in Matched Cohorts of Upper Airway Resistance and Obstructive Sleep Apnea Syndrome Patients". Chest.: 115; pp. 1519-1524.
Olga Para et al (2000). "Time Course of Sleep-related Breathing Disourders in First-Ever Stroke or Transient Ischemic Attack". American Journal Respiratory & Critical Care Medicine; 161; pp. 375-380.
G.N. Willson et al (2001). "Noninvasive Pressure Present Ventilation for the Treatment of Cheyne-Stokes Respiration During Sleep". European Respiratory Journal; 17; pp. 1250-1257.
T. Kohnlein etal (2002). "Assisted Ventilation for Heart Failure Patients with Cheyne-Stokes Respiration". European Respiratory Journal; 20; pp. 934-941.
Thomas Brack (2003). "Cheyne-Stokes Respiration in Patients with Congestive Heart Failure". Swiss Medical Weekly; 133; pp. 605-610.
Clodagh M. Ryan et al (2005). "Periodicity of Obstructive SLeep APnea in Patients with and without Heart Failure". Chest; 127; pp. 536-542.
Tadao Hori et al (2001). "Proposed Supplements and Amendments to 'A Manual of Standardized Terminology and Techniques and Scoring System for Sleep Stages of Human Subjects', the Rechtschaffen & Kales (1968) Standard". Psychiatry and Clinical Neurosciences; 55; pp. 305-310.
T. Shochat et al (2002). "The SleepStrip TM: an Apnoea Screener for the Early Detection of Sleep Apnea Syndrome". European Respiratory Journal; 19; pp. 121-126.
Examination Report, New Zealand Application No. 593988, New Zealand Patent Office, Jul. 15, 2011.
Chinese Office Action for corresonding application No. 200580044321.0; Aug. 22, 2008.
Chinese Office Action for corresonding application No. 200580044321.0; Aug. 7, 2009.
Chinese Office Action for corresonding application No. 200580044321.0; Jan. 22, 2010.
Chinese Office Action for corresonding application No. 200580044321.0; Apr. 29, 2010.

* cited by examiner

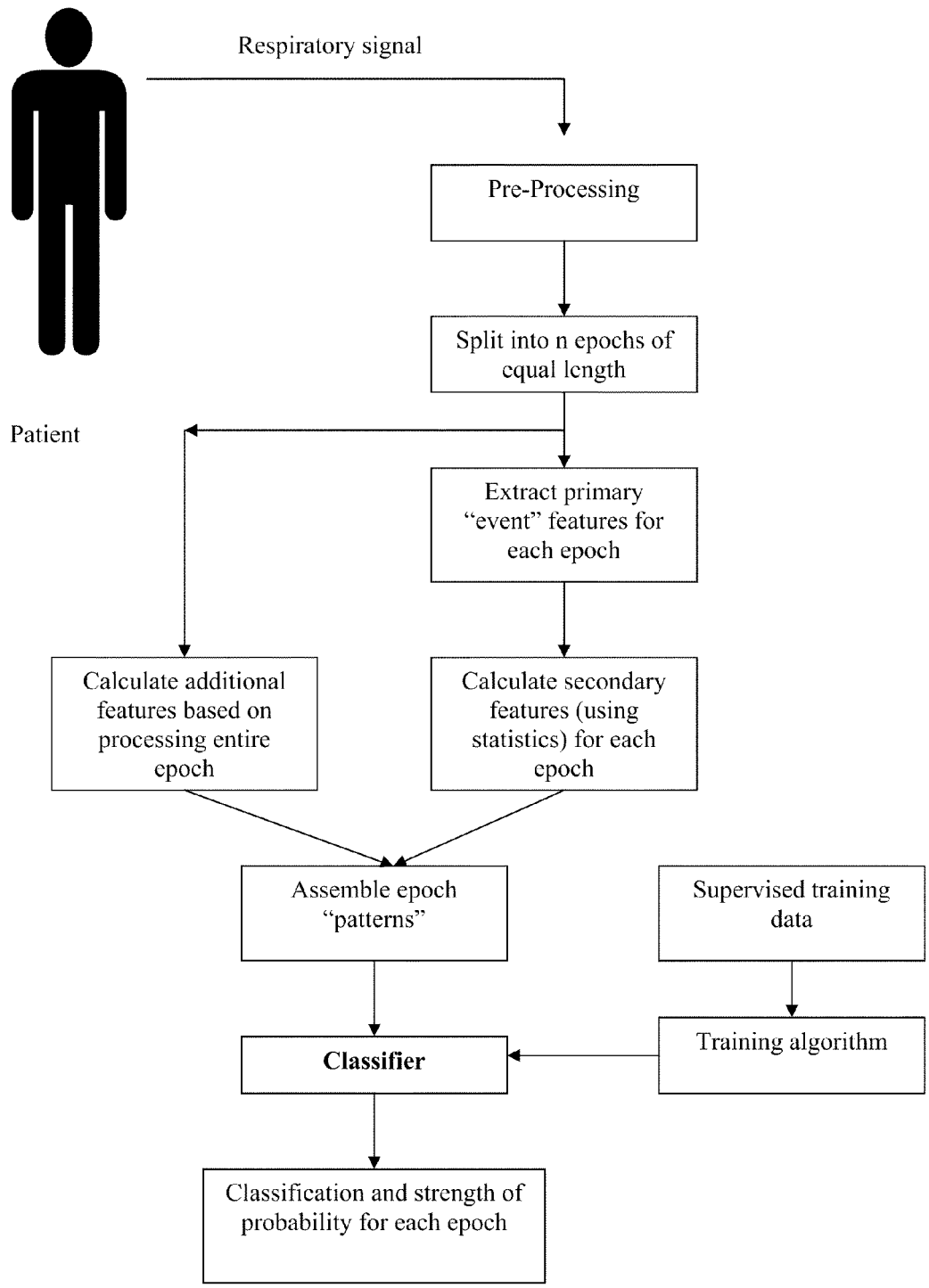
Figure 1: Log (max-jump feature)

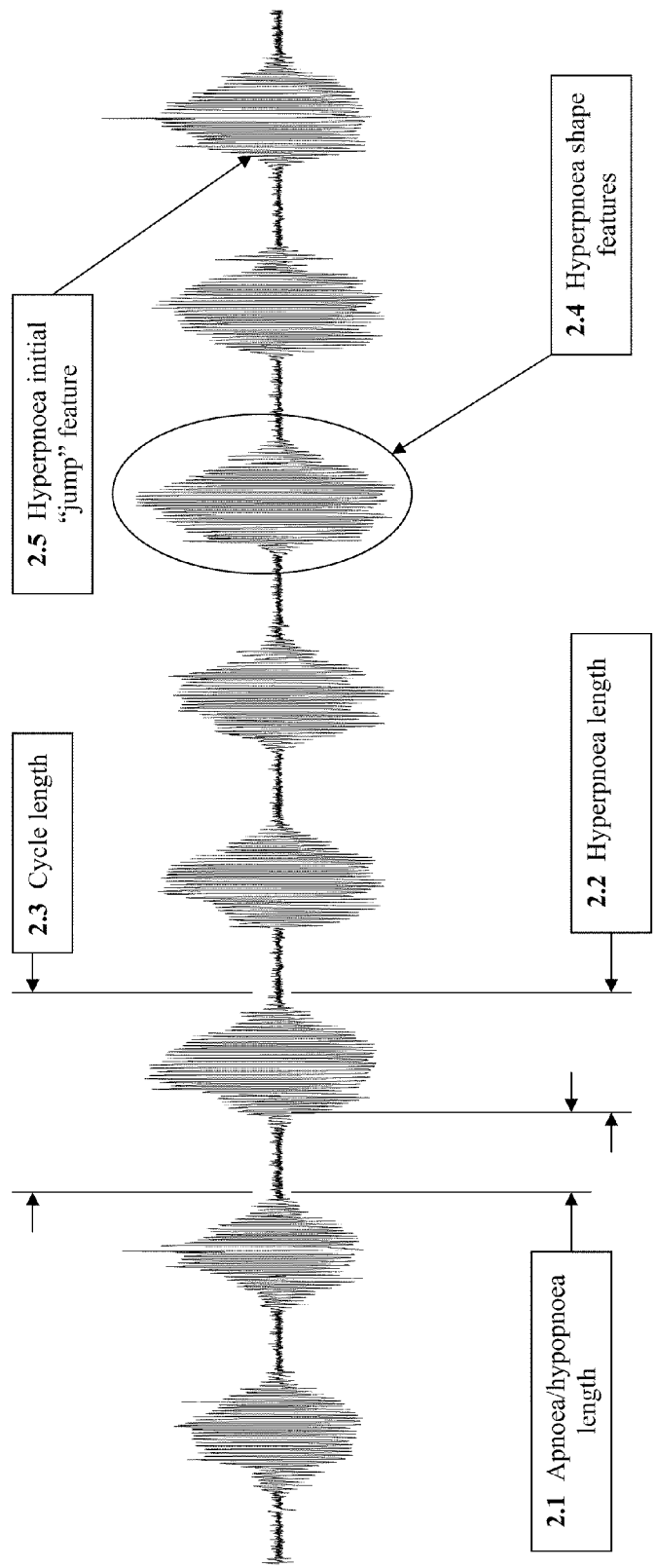
Figure 2: Epoch primary features.

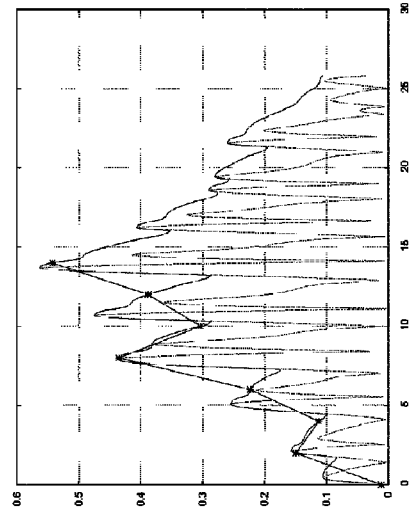
3.3 Calculation of the jump feature for an hyperpnoea typical of CS breathing.
(jump feature = 1.28,
shape features = [2.71 0.01 0.03 0.10])
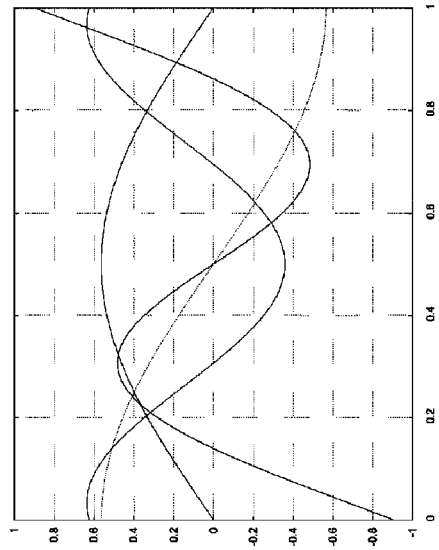
3.1 Basis functions used in determining hyperpnoea shape features
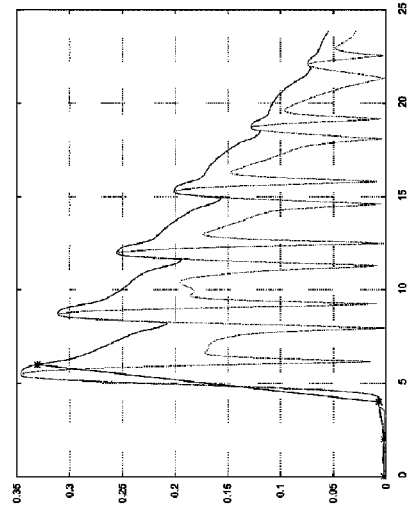
3.2 Calculation of the jump feature for an hyperpnoea typical of OSA.
(jump feature = 3.29,
shape features = [2.85 0.13 0.58 −0.12])
Figure 3: Feature calculation

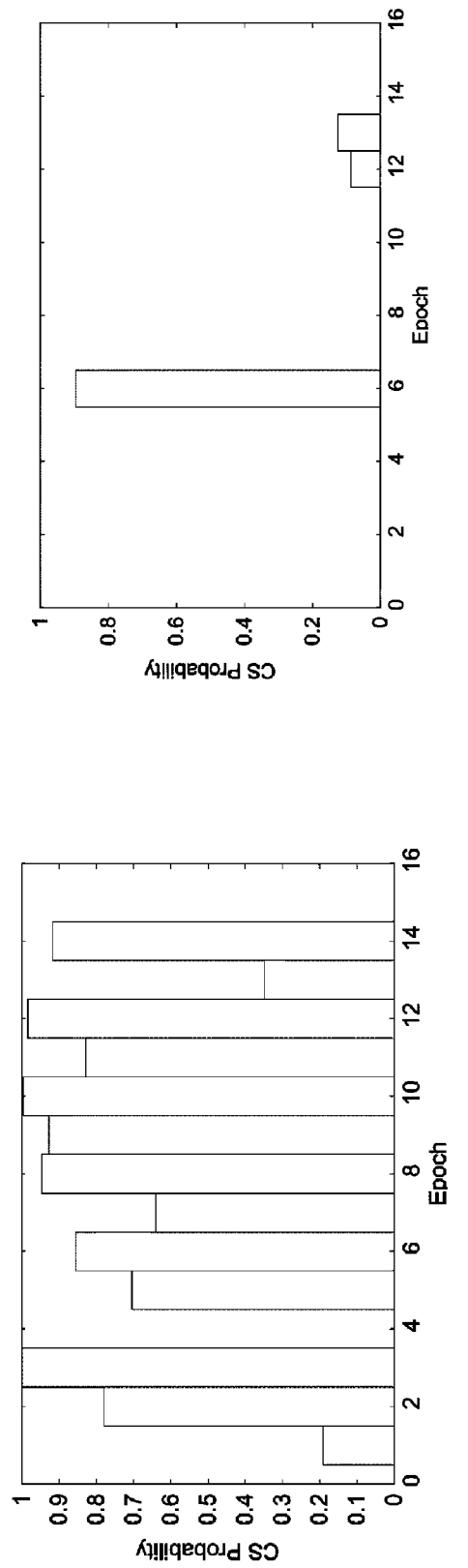
Figure 4: Reporting classification

CS= Cheyne-Stokes
O= Obstructive Sleep Apnea
MIX=Mixed Cheyne-Stokes and Obstructive Sleep Apnea

METHOD FOR DETECTING AND DISCRIMINATING BREATHING PATTERNS FROM RESPIRATORY SIGNALS

CROSS-REFERENCES TO RELATED APPLICATIONS

This application claims the priority of U.S. Provisional Patent Application 60/638,169, filed Dec. 23, 2004.

FIELD OF THE INVENTION

The present invention relates to methods, algorithms and diagnostic apparatus for the detection of sleep disordered breathing patterns and the discrimination between patterns of different disease states such as obstructive sleep apnea, central sleep apnea and Cheyne-Stokes breathing and mixed sleep apnea.

BACKGROUND OF THE INVENTION

Breathing Disorders

Sleep-disordered breathing (SDB) encompasses a group of disorders where the breathing pattern or quality of ventilation is abnormal during sleep. Obstructive sleep apnea (OSA), the most common such disorder (effecting possible 4-5% of the adult population), is characterized by repetitive closing or collapse of the upper airway and partial or complete diminution of breathing. The obstruction is normally ended by the patient arousing briefly when the muscles of the upper airway act to clear the obstruction. During the repetitive cycle of obstruction and arousal, the OSA patient will always continue to make "efforts" to breath; in other words there is no central or brain-mediated disruption to the breathing cycle.

Conversely, in central sleep apnea (CSA), there is a disruption to breathing which is brain or control-centre in origin. Cheyne-Stokes breathing (CS) is one of the more common forms of CSA. It is caused by an abnormal limit cycle instability of the patient's respiratory controller in which there are rhythmic alternating periods of waxing and waning ventilation. Patients with cardiac failure (a condition where the heart fails to pump adequately) often have CSA, especially as the condition deteriorates or where therapy has ceased to allow effective compensation by the heart. Cheyne-Stokes breathing appears as a cyclical variation in tidal volume seen in heart failure patients. The cycle consists of an apnoea or hypopnoea followed by an overshooting hyperpnoea which often (but not always) has a characteristic hump backed morphology s a.k.a. a "Sydney Harbor Bridge" shape. The exact cause of CS breathing is not fully understood. However, the characteristic waxing and waning cycle is strongly reminiscent of limit cycles in a poorly adjusted control system with a maladjusted gain or destabilizing feedback-loop delay.

Sleep-disordered breathing is undesirable in all its forms because it disrupts sleep architecture (the pattern and proportion of the different forms of sleep) leading to daytime somnolence. The repetitive cessation or diminution of ventilation causes (sometimes dramatic) drops in blood oxygenation levels. These and other complications are probably responsible for the now established sequelae of cardiovascular conditions.

The treatment of choice for OSA is continuous positive airway pressure (CPAP) as first described by Sullivan [Sullivan C E, et al. Reversal of obstructive sleep apnea by continuous positive airway pressure applied through the nares. *Lancet* Apr. 18, 1981 ;1(8225):862-5]. CPAP is also used to treat some heart-failure patients with CSA and congestive heart failure (fluid on the lungs). However, Cheyne-Stokes breathing is ineffectively treated by CPAP and may require the application of servo-ventilation [Teschler H et al. Adaptive pressure support servo-ventilation: a novel treatment for Cheyne-Stokes respiration in heart failure. *Am J Respir Crit Care Med.* Aug. 15, 2001; 164(4):614-9. Berthon-Jones Ventilatory assistance for treatment of cardiac failure and Cheyne-Stokes breathing. U.S. Pat. No. 6,532,959].

Diagnosis from Multiple Signals

The gold standard for the diagnosis of SDB and sleep apnea is the polysomnograph (PSG): the measurement and recording of a multitude of physiological signals during a stay overnight in a sleep laboratory. Briefly, the PSG signal ensemble normally includes one or more signals indicative of a respiratory parameters such as patient airflow rate (for the calculation of ventilation and the detection of apneas and hypopnoeas), multiple electroencephalogram (EEG), electrooculogram (EOG) and electromyogram (EMG) signals (for the determination of patient sleep state, position and the detection of arousals from sleep), breathing effort signals (either chest and abdominal distension bands or an esophageal pressure-measuring catheter), snore amplitude, and oxygen saturation. Another method of diagnosing SDB is polygraphy (PG) whereby a reduced number of parameters are recorded while the patient sleeps. These parameters include: nasal/oral airflow rate, snore amplitude, oxygen saturation, respiratory effort (thoracic and abdominal) and body position.

In both the PSG and the PG a breathing-effort signal is recorded to enable the discrimination of OSA events from CSA or Cheyne-Stokes breathing. (A third type of event is also possible-the mixed apnea-where the event is initiated by a centrally-mediated lack of breathing drive and ends with an airway obstruction and subsequent arousal). It is impossible for the inexperienced observer to reliably determine the type of apnea without reference to at least the flow signal and a measure of breathing effort. However, an experienced and trained observer (expert) can often readily detect patterns in a run of events (apneas/hypopnoeas) allowing a reliable determination of the type of underlying disease. This is especially true of Cheyne-Stokes breathing which has a very characteristic waxing and waning pattern of ventilation.

Simple Recording Devices

The performance of either a PSG or PG requires trained technicians, is expensive, is time consuming and can itself introduce sleep disturbances. Also, it is well known that a shortage of sleep laboratories is hampering the diagnosis and treatment of current SDB patients, let alone what is considered a vast undiagnosed population. For these reasons a type of "screening" device (e.g., the MICROMESAN® from MAP of Germany, or the APNEALINK™ from ResMed) is available to test patients suspected of having sleep-disordered breathing. Such devices are small, recording just one or two physiological signals, and can be readily sent home with the patient for a screening study. For example: patients' nasal airflow can be recorded and later examined by a physician using a personal computer and a connection to the device. A software package would then be available to read the data from the device, show statistics and make recommendations regarding suspected sleep-related pathology.

Diagnosis Classifier

The calculation of the apnea-hypopnoea index (AHI, number of such events per hour on average) is a measure regularly used to guide the direction of either treatment or further investigation with a fill PSG or PG. A computer program or algorithm which further enables the discrimination between different underlying disease states based on the recorded breathing patterns provides added guidance to the clinical pathway. A strong indication of Cheyne-Stokes disease, for example, would suggest completely different follow-up compared to the more common forms of sleep apnea.

The concept of a classifier is common to many fields where it is desirable to assign an object or an underlying state of an object to one of a number of classes. This concept is used, for example, in the fields of voice recognition (where sound bytes are classified as different words or syllables), radar detection (where visual signals are classified as enemy/friendly targets) and medical diagnosis (where test results are used to classify a patient's disease state). The design of a classifier falls under the field of Pattern Recognition and a classifier can be of the supervised type (the classifier is built from training data which has been pre-classed by a supervisor or "expert") or unsupervised type (where the natural ordering or clustering of the data determines the different classes). Time signal classification usually relies on representing the signal at particular time points with "features". Features are simply numbers that distill the essence of the signal at a point in time, a form of compression. A set (or vector) of features is called a "pattern". A classifier takes a pattern and manipulates it mathematically with a suitable algorithm to produce a probability value for each of a number of classes. The pattern is assigned to the class with the highest probability.

In U.S. Pat. No. 6,839,581 there is disclosed a method for detecting CS respiration in patients with congestive heart failure by performing spectral analysis of overnight oximeter recordings to obtain a set of parameters that can be used in the construction of a classification tree and a trained neural network.

In summary, sleep-disordered breathing is a common syndrome with different underlying disease types requiring very different treatment options. There is a need for a small and relatively inexpensive screening devices that can help unblock the treatment bottleneck that currently exists at the sleep laboratory. An algorithm and diagnostic apparatus that can replicate the expert's ability to detect breathing patterns associated with particular disease states will enhance the diagnosis and treatment of patients being screened for sleep-disordered breathing, or for monitoring patients already undergoing therapy. What is needed is an algorithm for flow data in the form of classifier.

What is particularly desirable is a method and apparatus for diagnosing Cheyne-Stokes breathing from flow readings or oximeter readings by use of appropriate software in conjunction with a small hand-held device for use in a home setting.

BRIEF SUMMARY OF THE INVENTION

The CS diagnosis system of the present invention uses pattern classification techniques on a digital computer to identify periods of CS-like breathing by examining the flow signal alone. Ordinarily the definitive diagnosis of CS breathing relies on an "effort" signal, either esophageal pressure or an elastic band signal from the abdomen or thorax. An absence of effort denotes a central apnoea which may otherwise be difficult to distinguish from an obstructive apnoea or a mixed apnoea. A mixed apnoea is comprised of a central beginning (without effort) followed by a section of obstructed breaths once drive returns.

APNEALINK™ nasal flow data without other channels is processed to classify it as unambiguously Cheyne-Stokes (CS) breathing or nearly so and to then display a likely record to the physician for quick expert confirmation. An APNEALINK™ recorder is a single channel battery-powered respiratory pressure sensor system and provides recordings of respiratory pressure during sleep. The APNEALINK™ is a small (hand held) device manufactured by ResMed, designed for use in a home setting where it is worn strapped to the patient's chest. The device only records nasal flow (indirectly) using a nasal pressure-sensing catheter. All relevant respiratory information during sleep will be collected via nasal pressure cannula. This will allow cardiologists to manage such patients more expediently. For example, CS patients would go on to a full polysomnogram (PSG) workup for possible AutoSet CS therapy as appropriate. Non-CS patients might just go on to AutoSet to treat the underlying OSA as appropriate. After suitable offline processing of the nasal flow signal using a PC, the following events can be detected and displayed: apnoeas, hypopnoeas, flow-limitation and snore.

Cheyne-Stokes Detection Algorithm

The CS-detection algorithm uses the nasal flow signal from a device such as ResMed's APNEALINK® or other signal indicative of at least one respiratory parameter together with pattern recognition techniques to assign a probability of CS breathing to each 30 minute epoch of flow recorded. This invention details the initial filtering and "event" detection, where events are defined as regions of hypopnoea-hyperpnoea sequence characteristic of CS breathing. The detection of such events may be determined from the duration of one or more regions of hyperpnoea when the duration of the hyperpnoea exceeds a threshold or a statistic of the duration of regions of hyperpnoea exceeds a threshold. Such a statistic may be an average or a standard deviation or other statistics specified below.

Pattern classification techniques are statistical and rely on a so-called "training" data set by which a "classifier" can be trained to recognize certain "patterns", in this case CS breathing. A pattern is a group or vector of features. A feature is a number which represents some aspect of the signal being examined. An example of a feature is apnoea length. A pattern might be the group comprising apnoea length, hyperpnoea length and a number representing the closeness of the shape of the hyperpnoea to a "harbor bridge".

One aspect of the invention is directed to a method and apparatus or system capable of better diagnosing the presence of sleep disorders, preferably with a higher level of confidence. The diagnosis may comprise analyzing a signal indicative of a respiratory parameter to determine a rate of increase of the signal in the region from hypopnea to hyperpnoea and where the rate of increase is a slow increase, concluding that Cheyne-Stokes breathing is present and where the rate of increase is a sudden increase, concluding that Cheyne-Stokes breathing is absent.

According to one aspect of the invention, a signal representative of a patient's respiration is split into equal length epochs which can be as long (the entire record) or as short (the length of a representative hypopnoea-hyperpnoea sequence) as desired. Preferably, the signal will be subject to a number of pre-processing steps in order to filter out noise and zero the baseline, for example.

Preferably, from each epoch one or more primary features is extracted from the signal that act as a compressed representation of the signal events. By events it is meant: e.g., apneas, hypopnoeas and hyperpnoeas. Statistics are applied to the primary feature(s) to produce one or more secondary features which represent the entire epoch. Each secondary feature is grouped with one or more other features that is extracted from the entire epoch rather than from the epoch events. This final group of features is the epoch pattern.

The epoch pattern is preferably manipulated with a suitable classifier algorithm to produce a probability for each possible class that the signal may be representative of (e.g. Cheyne-Stokes breathing, OSA etc.). The epoch is assigned to the class with the highest probability and the class and the strength of the probability can be reported as an indication of the underlying disease state.

The classifier algorithm is preferably learned from a training data set which has been pre-classified by a human expert. In this sense the classifier is of the supervised machine learning type.

BRIEF DESCRIPTION OF THE DRAWINGS

FIG. 1 is a block diagram of the signal processing pathway leading from the patient's respiratory signal through pre-processing, feature extraction based on epochs, through to classification.

FIG. 2 shows a typical respiratory signal epoch including a number of "events" (in this case apnea-hyperpnoea sequences). Several primary features are either shown explicitly (2.1 apnea/hypopnoea length, 2.2 hyperpnoea length, 2.3 cycle length) or inferred (2.4 shape features of the hyperpnoea, 2.5 a feature representing the initial "jump" at the beginning of the hyperpnoea).

FIG. 3 shows details of the calculation of primary features. 3.1 shows the basis fictions used in the determination of the hyperpnoea shape features. 3.2 shows an hyperpnoea typical of OSA together with the calculation of the jump feature displayed graphically. 3.3 shows a similar depiction of an hyperpnoea more typical of CS breathing. In both cases the calculated jump features and shape features are tabled.

FIG. 4 shows examples of epoch classification, e.g., using bar charts.

DETAILED DESCRIPTION OF PREFERRED EMBODIMENTS

Process Description

Figure 5:
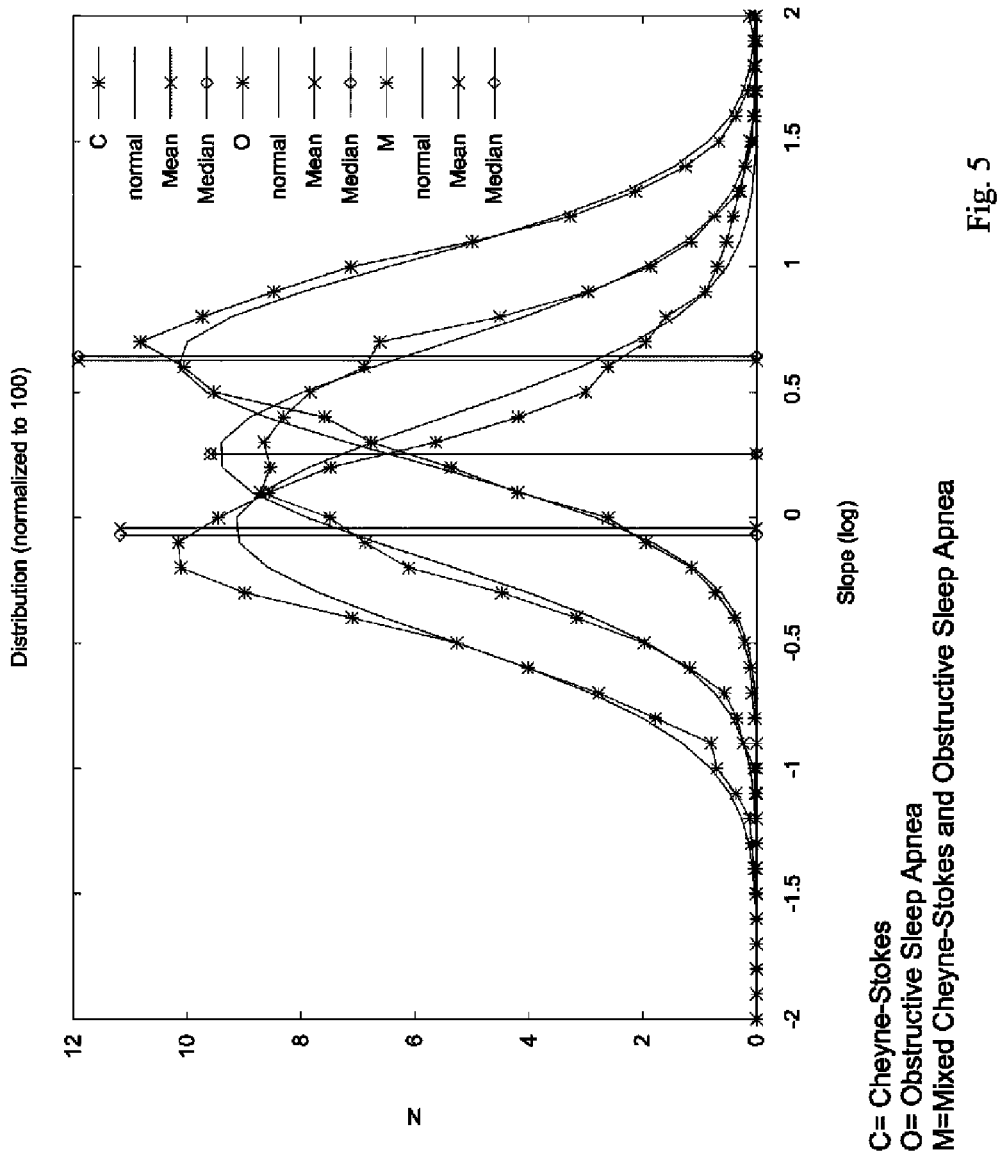
FIG. 5 shows the distribution of the normalized max jump in a hyperpnoea signal.

FIG. 1 shows one embodiment of the classification process. While the following may be explained in terms of a sequential process; it is understood that the process can be carried out using a non-linear, non-sequential, or non-staged process, or the order of the process may be changed. Also, while FIG. 1 describes an entire process, aspects of the invention may relate to only a subset of that process. A signal representative of respiration is first recorded from a patient using a logging device which includes a data-acquisition system and a memory. The respiratory signal is then processed either on-board by the recording device or off-line using a computer.

Preferably, the signal is initially pre-processed. For example, the signal is filtered to remove unwanted noise and, where appropriate, the baseline is zeroed. The signal may also be linearised depending on the transducer used to detect the respiration.

In the next stage the signal is divided into n epochs of equal length. The epoch length can be as long as the entire record or as short as is practicable to enable detection of respiratory patterns. In one preferred embodiment the epoch length is 30 minutes.

FIG. 2 shows a typical epoch recording in a patient with Cheyne-Stokes breathing. The shape of the curve is reminiscent of the shape of the Sydney Harbor Bridge and is sometimes referred to by that name. See also FIG. 10. The recording consists of five "events", each event consisting of a hypopnoea (in this case also an apnea) followed by a hyperpnoea. For each event an algorithm is used to detect the beginning and end points such that event lengths can be calculated: e.g., apnea/hypopnoea length and hyperpnoea length. A further algorithm may be used to reject events if they do not follow the correct sequence of hypopnoea/apnea hyperpnoea. Another further algorithm may be used to reject events that fall outside sensible length scale limits.

Determination of Shape Features

Each hyperpnoea is further processed to derive four so-called "shape features". These features indicate different shaped hyperpnoeas (bell-shaped versus triangle-shaped for example). The shape features are calculated using singular value decomposition of the hyperpnoea ventilation signal as follows: First, the hyperpnoea is extracted from the respiratory signal and the absolute value is taken of the respiratory signal, giving a ventilation signal. The ventilation signal is scaled by its mean value to give a vector of values $V_{hyperp}$. For mathematical convenience the time base of the hyperpnoea [0 . . . T], where T is the end of the hyperpnoea, is mapped to the interval [0 . . . 2π]. A set of four orthogonal functions are calculated and arranged as a 4×m matrix (where m is the number of values in the hyperpnoea signal). A convenient set of orthonormal function are:

$$M_{Basis} = \begin{pmatrix} \frac{1}{\sqrt{\pi}}\sin\left(\frac{t}{2}\right) \\ \frac{1}{\sqrt{\pi}}\cos\left(\frac{t}{2}\right) \\ \frac{\left(3\pi\sin(t) - 8\cos\left(\frac{t}{2}\right)\right)}{\sqrt{\pi(9\pi^2 - 64)}} \\ \frac{\left(3\pi\cos(t) + 4\sin\left(\frac{t}{2}\right)\right)}{\sqrt{\pi(9\pi^2 - 16)}} \end{pmatrix}$$

where t is the time base over the hyperpnoea from 0 to 2π. The basis functions are shown plotted in figure 3.1. The four shape features are then calculated as:

$$F_{P(1-4)} = V_{hyperp} \times \text{PseudoInverse}(M_{Basis}),$$

and are normalized by:

$$F_{P(1-4)} = \frac{F_{P(1-4)}}{L_2|F_{P(1-4)}|}$$

where $L_2\|$ is the L2 or Euclidean norm., $$\sqrt{\sum_i^n x_i^2}$$

The pseudoinverse $M^+$ of a matrix M is a generalization of a matrix inverse, and exists for any (m,n) matrix M (for convenience assume m>n). If such a matrix M has full rank (n) one defines: $M^+=(M^TM)^{-1}M^T$. The solution of Mx=b is then $x=M^+b$. (Pseudoinverses are useful because of a general theorem stating that $F=M^+v$ is the shortest length least squares solution to the problem MF=v.)

Jump Determination

Since sudden jumps in the ventilation/flow at the beginning of an hyperpnoea are characteristic of OSA, (see FIG. 2) each hyperpnoea is further processed to derive the so-called "jump" feature, indicative of the extent of any sudden increase in flow, as follows: Again, the hyperpnoea is extracted from the respiratory signal, the absolute value is taken of the respiratory signal, giving a ventilation signal, a droopy peak-detector is used to approximate the envelope of the ventilation signal:

$$e[1] = v[1]$$
$$\text{for } i = 2 \ldots m$$
$$\text{if } v[i] \geq e[i-1]$$
$$e[i] = v[i]$$
$$\text{else}$$
$$e[i] = e[i-1] + \frac{1}{2.5 f_s}(v[i] - e[i-1])$$
$$\text{end}$$

where e[i] is the approximate envelope, $f_s$ is the sampling frequency and v[i] is the ventilation signal. The envelope is interpolated over a new two-second time base (chosen to be roughly the time-length of a breath) to give $e_1$ (between non-breathing intervals). The maximum positive difference $e_{1i} - e_{1(i-1)}$ (over the two second interval) is found in the interpolated signal in the interval between the beginning of the envelope and the point at which the envelope attains its maximum value. Finally, the maximum difference is scaled by the mean value of the ventilation signal to give the "jump feature". Figures 3.2 and 3.3 show this process graphically for two representative hyperpnoeas.

Secondary Feature Determination

Secondary features are calculated from primary features using the (measure of variation) statistics detailed below. (Note log denotes the logarithm to base e.) First we define the standard deviation as:

$$STD(F_P) = \sqrt{\frac{1}{n-1} \sum_{i=1}^{n} (F_{Pi} - \overline{F_P})^2}, \text{ where } \overline{F_P} = \frac{1}{n} \sum_{i=1}^{n} F_{Pi}$$

For length measures (e.g. hypopnoea length) and the jump feature the four features are:

1. $\frac{1}{n} \sum_{i=1}^{n} \log(F_{Pi})$

2. $\log(STD(\log(F_P)))$

3. $\log\left(\sqrt{\frac{1}{n} \sum_{i=1}^{n} (F_{Pi} - F_{P(i-1)})^2}\right)$ (To get a normed deviation)

4. $\log(STD(F_{Pi} - F_{P(i-1)}))$

For hyperpnoea shape features the four features are:

1. $\frac{1}{n} \sum_{i=1}^{n} (F_{Pi})$

2. $\log(STD((F_P)))$

3. $\log\left(\sqrt{\frac{1}{n} \sum_{i=1}^{n} (F_{Pi} - F_{P(i-1)})^2}\right)$

4. $\log(STD(F_{Pi} - F_{P(i-1)}))$

Additional Feature Determination

Additional features can be calculated using the entire (e.g. 30 minute) epoch signal. One such feature is derived from the spectrogram of the epoch signal and determining that Cheyne-Stokes breathing is present if the spectrogram indicates that the signal has a peak. This feature is calculated as follows: First, the mean of the respiratory signal is calculated and subtracted from the respiratory signal and the resulting signal is chopped into n slices which overlap each other by exactly half the slice length. Each slice is next windowed, preferably using a Hanning window (to reduce edge effects).

The use of a Hanning window to prepare the data for a FFT is as follows: The FFT function treats the N samples that it receives as though they formed the basic unit of a repetitive waveform: It assumes that if one took more samples they would repeat exactly, with the (N+1) sample being identical to the first sample, and so on. The usual case is that if one's N samples start at one point in a cycle, they end at some other point, so that if one really did play these back in a loop one would get a discontinuity between the last sample and the first. Hence one tapers both ends of the set of samples down to zero, so they always line up perfectly if looped. The formal name for this process is "windowing", and the "window function" is the shape that we multiply the data by. When the window function is the "raised cosine" 1+cos t the window is termed a Hanning window. Other periodic functions can be used, yielding other windows.

Next, since CS data appears periodic, a fast Fourier transform is applied to each windowed slice, yielding a complex vector result for each slice. The absolute value is taken of each complex result yielding a real valued vector per slice. The mean is taken of the resulting vectors to yield one vector. The natural log is taken of the subsequent vector and the values in the frequency range 0 Hz to 0.075 Hz are extracted to form a sub-vector, which is then de-trended. Cheyne-Stokes behavior is present if the spectrogram indicates the signal has a peak in the range 0 Hz to 0.075 Hz.

Briefly, the method of detrended fluctuation analysis is useful in revealing the extent of long-range correlations in time series, where the time series is a vector of data pairs $(t_i, x_i)$, where t represents time and x represents the variable being measured. De-trending consists of subtracting from the x values, values that have been calculated using a polynomial of order n that has been fitted to the data. For example, for order zero the polynomial is simply the mean of all the x values, and that mean is subtracted from the original values. For order one, the polynomial is simply a linear fit to the data $(t_i, x_i)$. Values calculated using the best linear fit are then subtracted from the original values (so removing any linear "trend"). For order two the fitted polynomial is a quadratic, for order three a cubic etc.

The feature is then calculated as the maximum minus the mean of the de-trended vector. Alternatively one could calculate the entropy of the FFT instead of its peak.

Additional features can be derived by applying wavelet analysis to each epoch. In this case wavelet coefficients or statistics derived from wavelet coefficients are used as features for the epoch. This yields the location of the peak in time. In wavelet analysis a wave packet, of finite duration and with a specific frequency, is used as a window function for an analysis of variance. This "wavelet" has the advantage of incorporating a wave of a certain period, as well as being finite in extent. A suitable wavelet (called the Morlet wavelet) is a sine wave multiplied by a Gaussian envelope.

Classification

A subset of features is then selected for use by the classifier. It is known that a particular subset of features can provide more accurate classification than the full set of features. This is caused in part by the so-called "curse of dimensionality", whereby the required number of training samples increases with the number of features used. The curse of dimensionality causes networks with lots of irrelevant inputs to behave relatively badly: Where the dimension of the input space is high, the network uses almost all its resources to represent irrelevant portions of the space.

An algorithm is employed to select the best subset based on the training data. Ideally every subset of features should be tested for accuracy and the best subset chosen. The number of subsets is $2^n-1$ where n is the number of features. Unless there is a small number of features the exploration of all subsets is impractical and, in any case, accuracy measures tend to be noisy which further hampers the search for the best subset. Alternative algorithms that enable selection of "good" feature subsets include "best first", "remove worst", "random start with add and remove", "simulated annealing" and genetic algorithms.

A method often used to measure accuracy is 10-fold cross-validation. The training data are split into ten groups or folds and ten different accuracy tests are performed. In each case 9 tenths of the folds are used for training and the resulting classifier is tested for accuracy on the remaining tenth. Statistics are performed on the 10 results to give a measure of accuracy.

Training the Classifier

Once a feature subset is chosen, the classifier is trained using the entire training data set. A number of classifier types are available including: Baysean maximum likelihood linear and quadratic discriminants, neural networks and support vector machines. In each case a discriminant function is calculated which, when applied to features calculated from new data to be classified, provides probability estimates for different classes. The data (epoch) is assigned to the class with the highest probability.

In one particular embodiment the discriminant function includes or preferably consists of two weight vectors (of the same length as the feature subset) and two constants. When the desired feature subset has been extracted from the respiratory epoch, the discriminant functions and probability are calculated as follows:

$$d_1 = W_1 \Box F + C_1$$

$$d_2 = W_2 \Box F + C_2$$

$$\text{probability} = \frac{e^{(d1-d2)}}{1 + e^{(d1-d2)}}$$

where $W_1$, $W_2$ are vectors and $C_1$, $C_2$ are constants.

The probability cutoff may be set at 0.5 in which case a probability of 1.0 would equate to class A and a probability of 0.0 to class B. The cutoff can be adjusted to suit the desired sensitivity and specificity. This is a two-way classification. With suitable training data, a three-way classification is also possible as are even higher n-way classifications.

In one particular embodiment the classification of each epoch could be displayed in a bar chart as in FIG. 4. Frame 4.1 shows a bar chart where many epochs show a high probability of a class of respiration (in this case CS-like breathing). This provides an "at-a-glance" indication of a patient record. Frame 4.2 shows a bar chart where only a single epoch displays strong CS-like tendency. This provides an indication of where in the patient's record a more detailed investigation is warranted.

Cheyne-Stokes Classifier Based on a Flow Signal or an Spo2 Signal or Both

The APNEALINK device is capable of measuring an estimate of a patient's flow signal which can be used as an input to the algorithm described herein. Equally there are similar portable devices that can measure and log SpO2, the saturation of oxyhemoglobin in the blood as estimated by pulse oximetry. Pulse oximetry is a simple non-invasive method of monitoring the percentage of haemoglobin (Hb) which is saturated with oxygen. The pulse oximeter consists of a probe attached to the patient's finger or ear lobe which is linked to a computerised unit.

SpO2 is typically reported as a percentage, values above 95% being normal and those below 95% indicating some degree of hypoxia (lack of oxygen in the blood). Should a patient undergo an apnoea or hypopnoea, it is usual for the SpO2 signal to fall concomitantly with the ventilation, albeit after some delay. During Cheyne-Stokes breathing the SpO2 signal will undergo the classic waxing and waning pattern also characteristic of the ventilation.

Hence, it is conceivable that the algorithm described herein might use a flow signal estimate (ventilation) or an SpO2 signal or both signals to classify breathing patterns as being typical of Cheyne-Stokes, OSA, mixed apnoeas etc.

Figure 12:
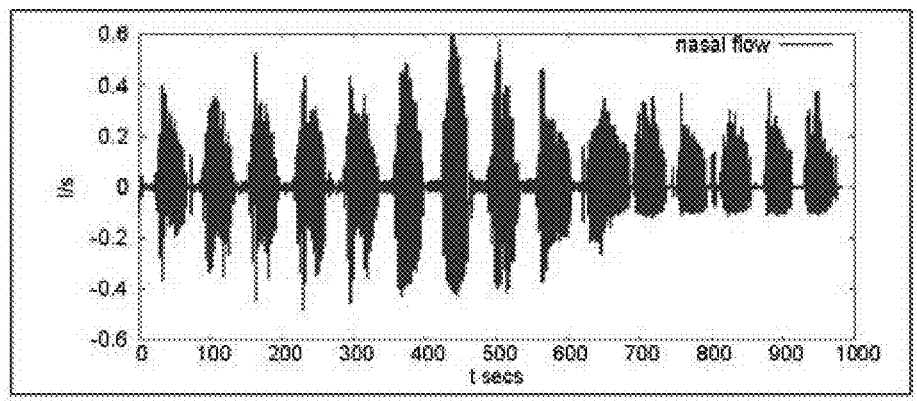
FIG. 12 shows a Cheyne-Stokes patient's nasal flow signal over about 15 minutes.
Figure 13:
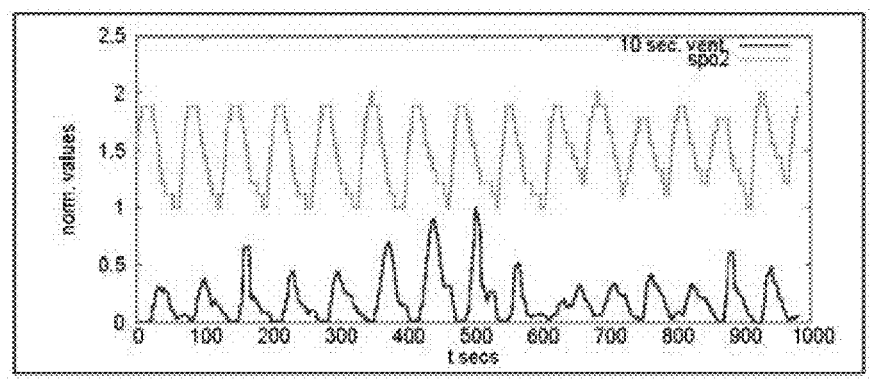
FIG. 13 shows a patient's SpO2 signal (saturation) and ventilation signal (low-pass filtered absolute value of flow).

FIG. 12 shows a Cheyne-Stokes patient's nasal flow signal over about 15 minutes. FIG. 13 shows the same patient's SpO2 signal (saturation) and ventilation signal (low-pass filtered absolute value of flow). The signals have been normalized and shifted to display them in the same graph. The same pattern recognition techniques may be applied to both signals. For example: segment the signal into hypopnoeas/hyperpnoeas; analyze the shape of the hypopnoeas; determine the cycle lengths and space ratios; perform a spectrogram (average of absolute value of a number of FFTs); determine peaks in the spectrogram at the CS frequency; determine a morphologic feature in both signals such as the jump feature; perform a continuous wavelet transform on both signals and use ridge finding techniques to follow any CS frequency component over time.

EXAMPLE 1

A set of data for testing the ability of flow data to be classified into OSA and CS instances consisted of 90 patient studies of approximately 8 hours each. For purposes of the test, both nasal pressure, flow and two effort signals (abdomen & thorax) were recorded, making a confirming diagnosis of the underlying disease possible. The set was divided into 3 groups of 30 patients: OSAi(obstructive apnoea), CS and Mixed. The data were further classified (initially) on a 30-minute time-bin basis. The time periods were classified into the following categories: No apnoeas or hypopnoeas (<5) within the time period; Primarily CS breathing (>90%); Primarily OSA (>90%); Primarily (>90%) apnoeas and hypopnoeas of mixed type (i.e. having a central component followed by a number of obstructed breaths); A combination of different events, typically brief periods of CS or mixed apnoeas interspersed between OSA; Patient is moving and the signal is of too low a quality to be useable.

Typically if CS disease is present, CS breathing will occur in large blocks of at least 20-30 minutes. The data set contained very few periods of "pure" mixed apnoeas. Rather, the mixed group of 30 patients contained periods of OSA, CS breathing or a mixed picture.

Feature Analysis

All features were analyzed by calculating distributions for the different groups (OSA, Mixed, and CS). The distribution was normalized by application of an appropriate function, for example FIG. 5 shows the distribution of the normalized max jump in hyperpnoea signal between beginning of hyperpnoea and time of peak flow after application of log-to-base-e. The leftmost curves represent a "normal" or Gaussian distribution. It can be seen that the application of the log function has normalized the distributions and, further, that this feature shows good separation between the CS (left) and OSA (rightmost) groups.

Cluster Analysis

Figure 6:
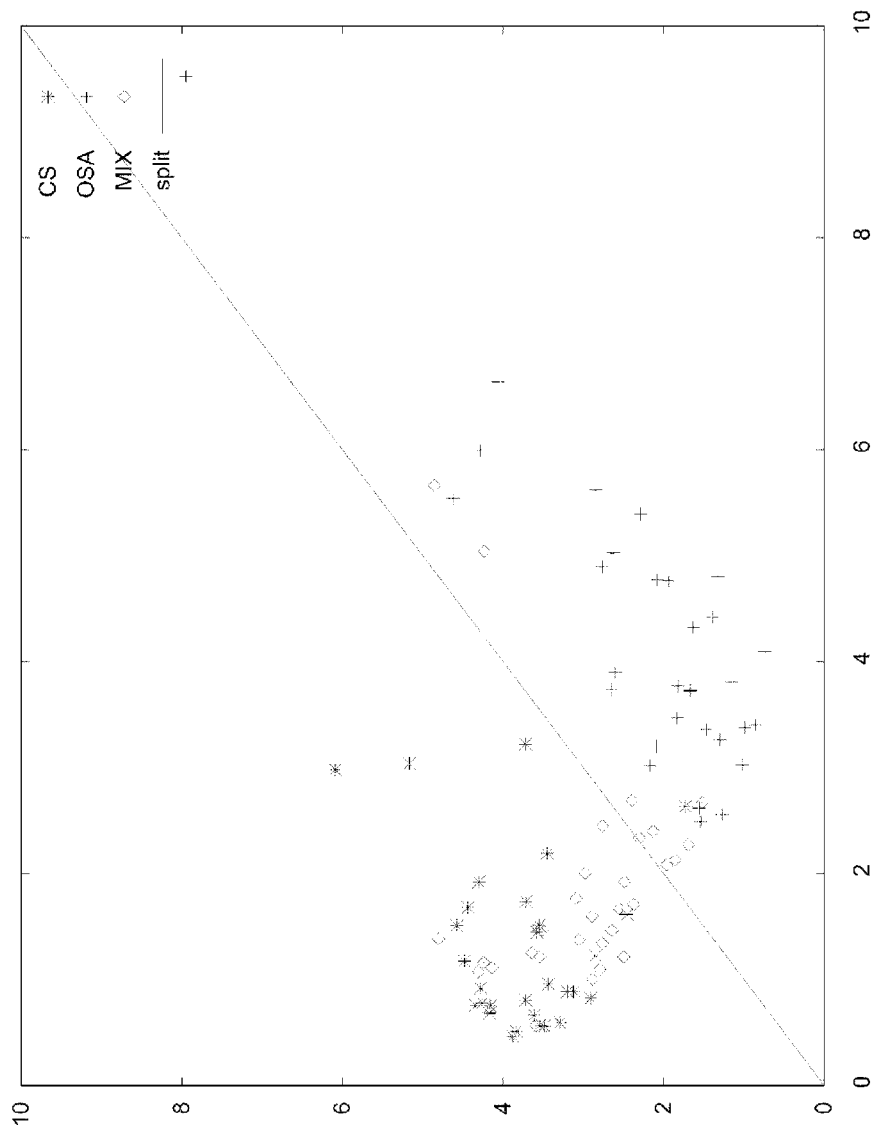
FIG. 6 shows a cluster analysis of CS and OSA patients.

Both k-means and fuzzy k-means clustering techniques were utilized to visualize feature separation power. The features were first averaged on a per-patient basis and then custer analysis was used to demonstrate a natural clustering into correct groups. FIG. 6 shows such an analysis. The Euclidean 2-norm distance from each of two cluster centers is plotted one against the other. The CS and OSA patients naturally fall into two groups except for one CS patient. The Mixed patients fall into one group or the other depending on the length of time spent during the night in different breathing patterns. The separating diagonal in the figure represents a naive classifier suitable for per-patient grouping. What such a classifier cannot do is find a short period of CS breathing from amongst an otherwise OSA-dominated night.

Feature Temporal Averaging

The training of a classifier using patterns assigned to individual events is problematical. Temporal averaging was used to reduce the amount of calculation, while also (potentially) increasing statistical power. A 30-minute time-bin was chosen as a best first-guess. After temporal averaging, a new set of per-time-bin patterns is created. The raw features used (visible separation of groups) were: hypopnoea length; hyperpnoea length; $1^{st}$ Fourier shape feature; $2^{nd}$ Fourier shape feature; and normalized max jump. The time-averaged 30-minute bin features tested were (std=standard deviation, meansq=mean of square of values, sqrt=square root, shift=allows calculation of temporal difference).

Classifier Training and Testing

Once the data had been processed and the "expert" diagnosis made, a group of 1440 30-minute bins was available for classifier training (90 patients×16 bins).

Classifier Selection

Numerous statistical methods exist for the training of a classifier from n-dimensional data, e.g.: nearest neighbor, neural nets, cluster analysis. However, because the data "appeared" linearly separable, Bayesian decision theory was used. This theory (which relies on underlying normal probability density functions) uses the minimization of the Bayes error to calculate a discriminant surface. Such a surface separates the data into one of n categories (in this case 2). Both linear and quadratic discriminant functions were utilized. The former separates the data with a hyperplane in m dimensions (where m is the number of features) while the latter separates the data with a hyperquadric. A hyperplane discriminant is always preferred (assuming accuracy of the same order), as it will tend to be well behaved in areas of minimal data coverage.

Over-optimistic Train and Test

Figure 7:
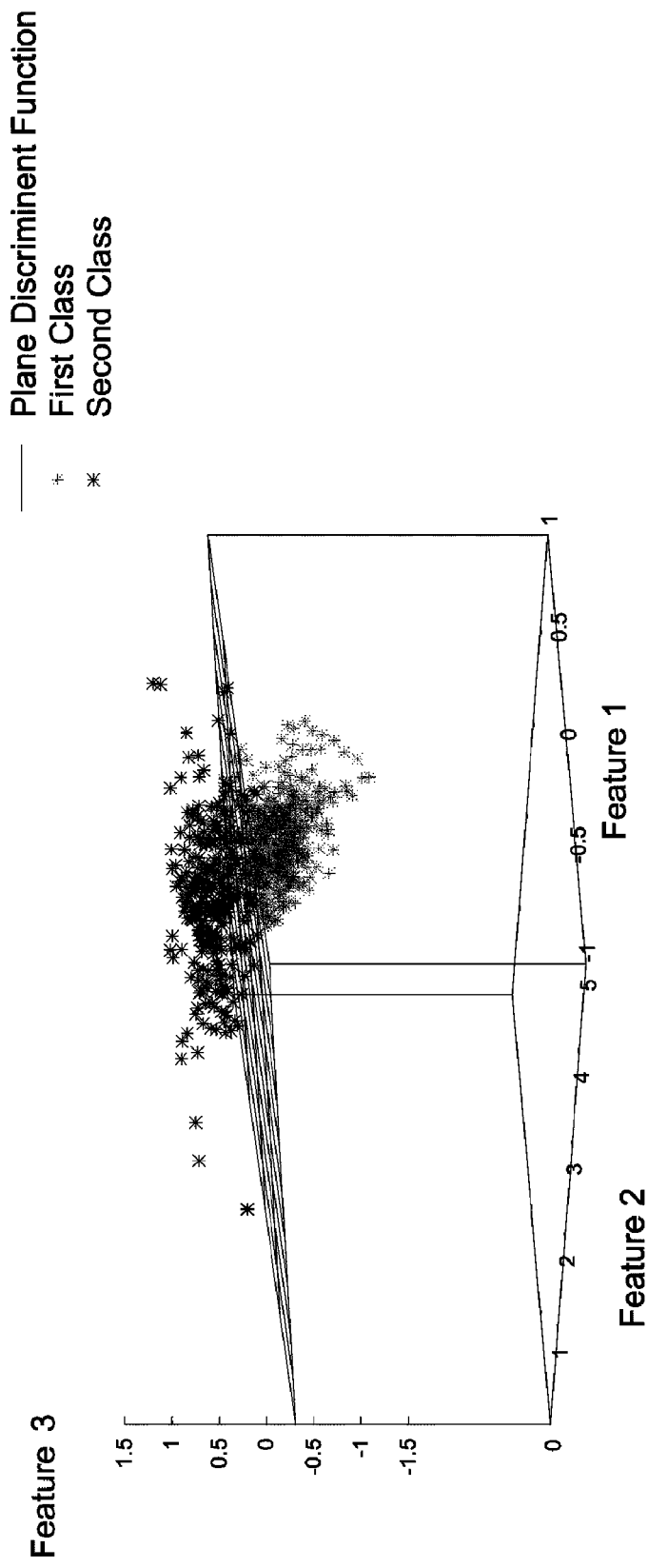
FIG. 7 shows results from a LD (linear) classifier.
Figure 8:
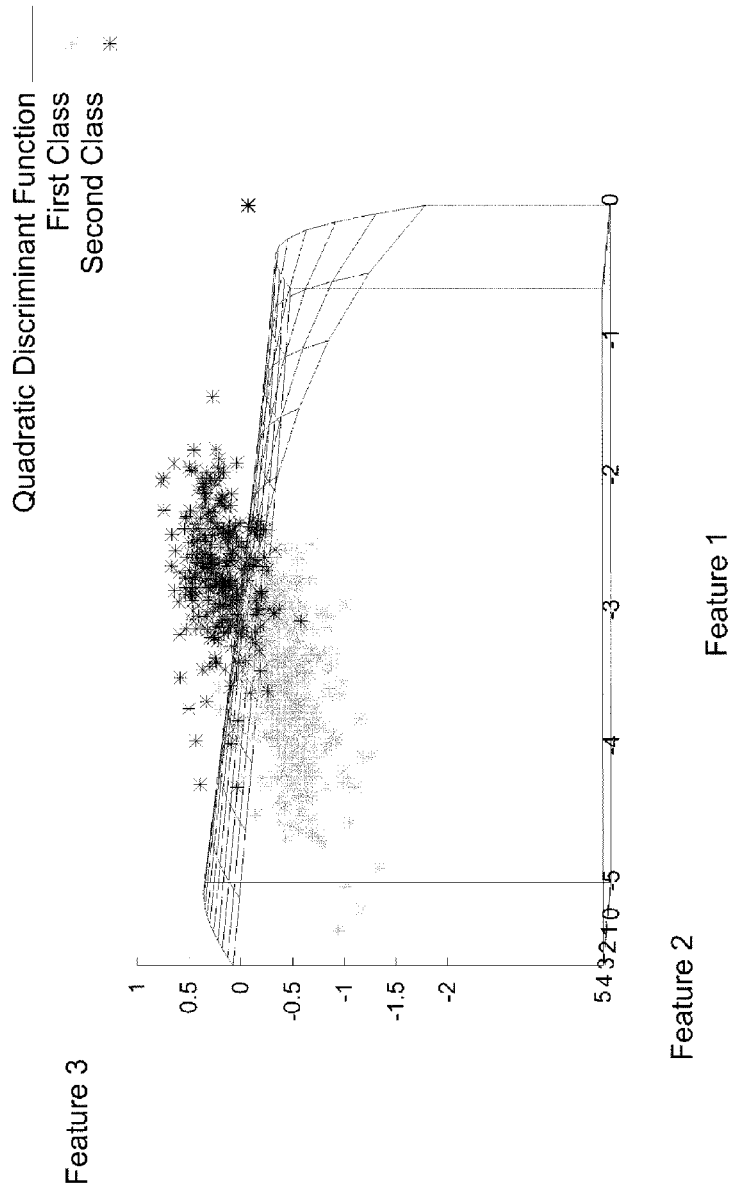
FIG. 8 shows results from a QD (quadratic) classifier.
Figure 9:
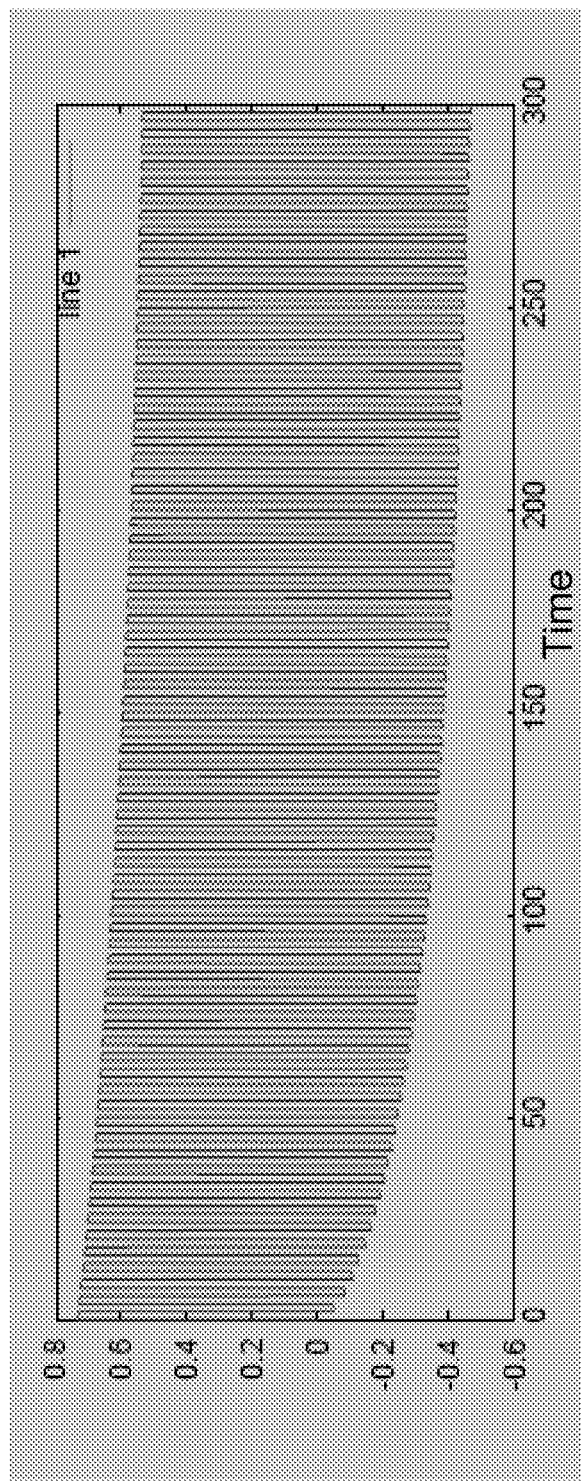
FIG. 9 shows the correction of data for baseline offset.

The classifier was trained using the training set and then the classifier was tested using the same data. This results in over-optimistic values of sensitivity and specificity, as one would intuitively expect. However, again this is an insightful process and one can use a minimal features set ($\leqq 3$ features) in order to visualize the result. FIG. 7 shows an LD classifier (plane shows equi-probability surface). FIG. 8 shows a QD classifier (quadric shows equi-probability surface).

Results

During each test the accuracy, sensitivity and specificity were noted as was the current features set (or group of feature sets) with the best accuracy. Estimates of accuracy, sensitivity and specificity resulted of the order of 91%, 91% and 96% respectively.

EXAMPLE 2

Flow Filtering

The flow is filtered first to remove unwanted and uninteresting high-frequency content. The filter used is a digital FIR (finite impulse response) filter designed using the Fourier method using a rectangular window. The filter has a pass-band from 0 to 0.9 Hz, a transition band from 0.9 to 1.1 Hz and a stop band above 1.1 Hz. The number of terms in the filter varies with sampling frequency. The flow signal is filtered by convolving the time series point-wise with a filter vector.

Ventilation Calculation

Figure 10:
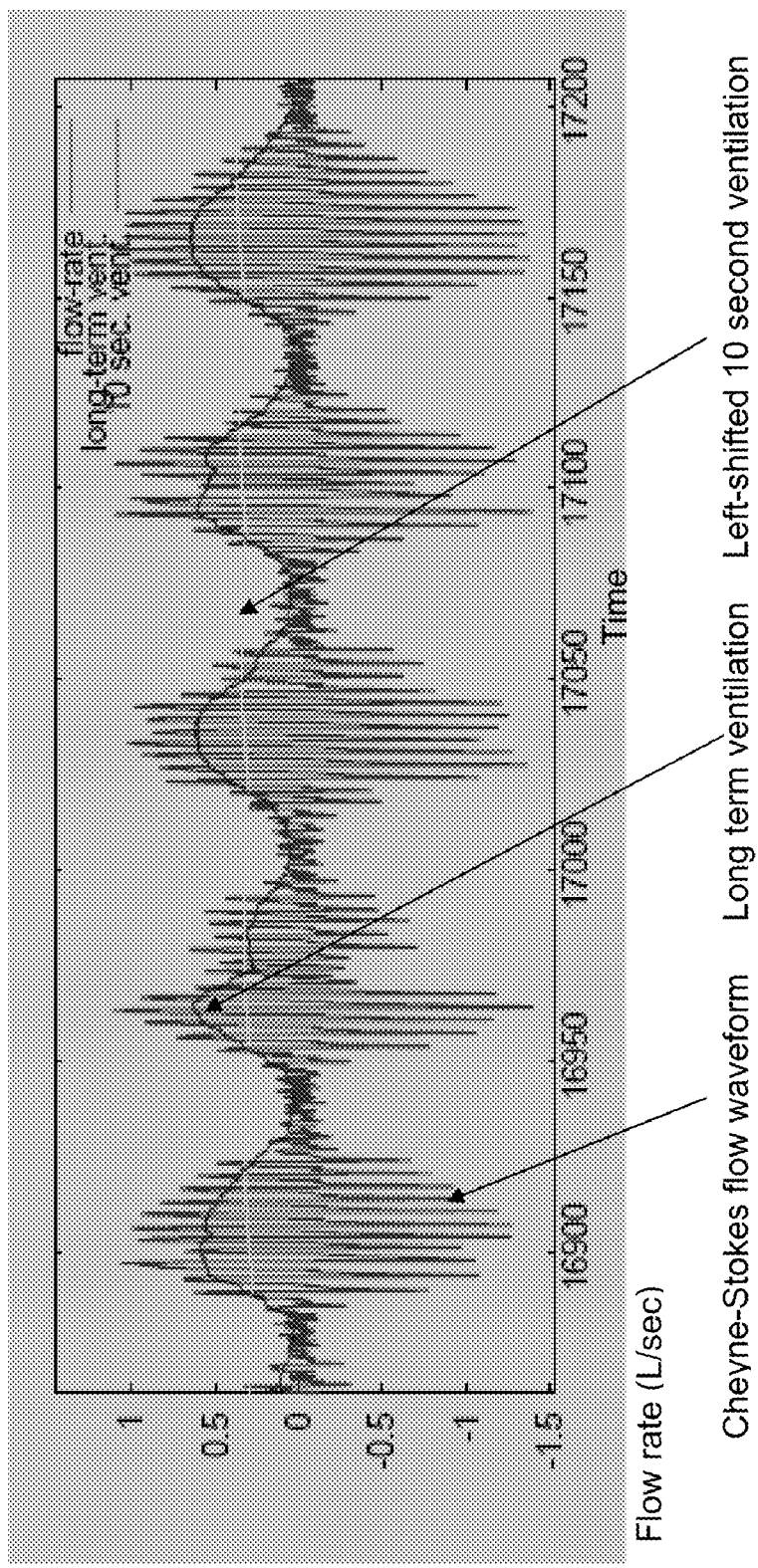
FIG. 10 shows a Cheyne-Stokes flow waveform, the long-term ventilation and the left-shifted 10-second ventilation for a typical patient.

A long-term ventilation signal $y_{long}$ is calculated using a simple (first order) low-pass filter applied to the flow signal. A time constant of 200 seconds is used (longer than the longest possible cycle of Cheyne-Stokes breathing). In order to measure ventilation (and not mean flow), the filter is applied to the square of the flow signal and the square root is taken of the filter output. Next, a ten-second ventilation $y_{10}$ is calculated (a more "recent" measure). This measure is created by convolving the square of the flow signal with a 10-second square wave with an area of one, i.e. a 10-second-long moving average, and then taking the square-root of the result. This filter will have a five second delay constant over the frequency range of interest. For this reason the signal is shifted left by five seconds so that it "lines up" with the original signal for timing purposes. FIG. 10 shows a Cheyne-Stokes flow waveform (large amplitude rapid varying curve), the long-term ventilation (low amplitude slowly varying curve) and the left-shifted 10-second ventilation (moderately varying curve) for a typical patient.

Event Detection from Ventilation Signals

The 10-second ventilation signal is used to create low and high thresholds for detection of events (hypopnoea-hyperpnoea sequences). The thresholds are:

$$thresh_{low} = 0.5 \times y_{long};$$

$$thresh_{high} = 0.75 \times y_{long};$$

The timing of events is calculated using the following algorithm:
1. Find all points where $y_{10} < thresh_{low}$.
2. Find all contiguous sections of the above points. These are provisional hypopnoeas.
3. Find all points where $y_{10} > thresh_{high}$.
4. Iterate over all of the hypopnoeas identified in step 2. If no points identified in step 3 (hyperpnoeas) fall between hypopnoea n and hypopnoea n+1, then the hypopnoeas n & n+1 are joined together (because no hyperpnoea has been identified between them) to form one hypopnoea. Repeat for all iterations.
5. The hypopnoeas are now confirmed. All inter-hypopnoea regions are considered hyperpnoeas. Each hypopnoea-hyperpnoea "event" constitutes one possible Cheyne-Stokes cycle. E.g. in FIG. 10 there are five cycles shown.

Calculate Event Timings

Event timings are calculated for each event as follows:

$$\tau_{hypopnoea} = t(end\_of\_hypopnoea) - t(beginning\_of\_hypopnoea);$$

$$\tau_{cycle} = t(beginning\_of\_next\_hypopnoea) - t(beginning\_of\_hypopnoea);$$

$$\tau_{hyperpnoea} = t_{cycle} - t_{hypopnoea};$$

Obviously the above events will include some unwanted "garbage". For example, a one-hour-long period of normal breathing bracketed on each side by Cheyne-Stokes breathing will look like a one-hour-long hyperpnoea! (y10 always greater than threshold). Hence, the following sensible limits are applied to the events:

$\tau_{hypopnoea}$: minimum=10 seconds, maximum=100 seconds,
$\tau_{cycle}$: minimum=15 seconds, maximum=250 seconds,
$\tau_{hyperpnoea}$: minimum=5 seconds.

Figure 11:
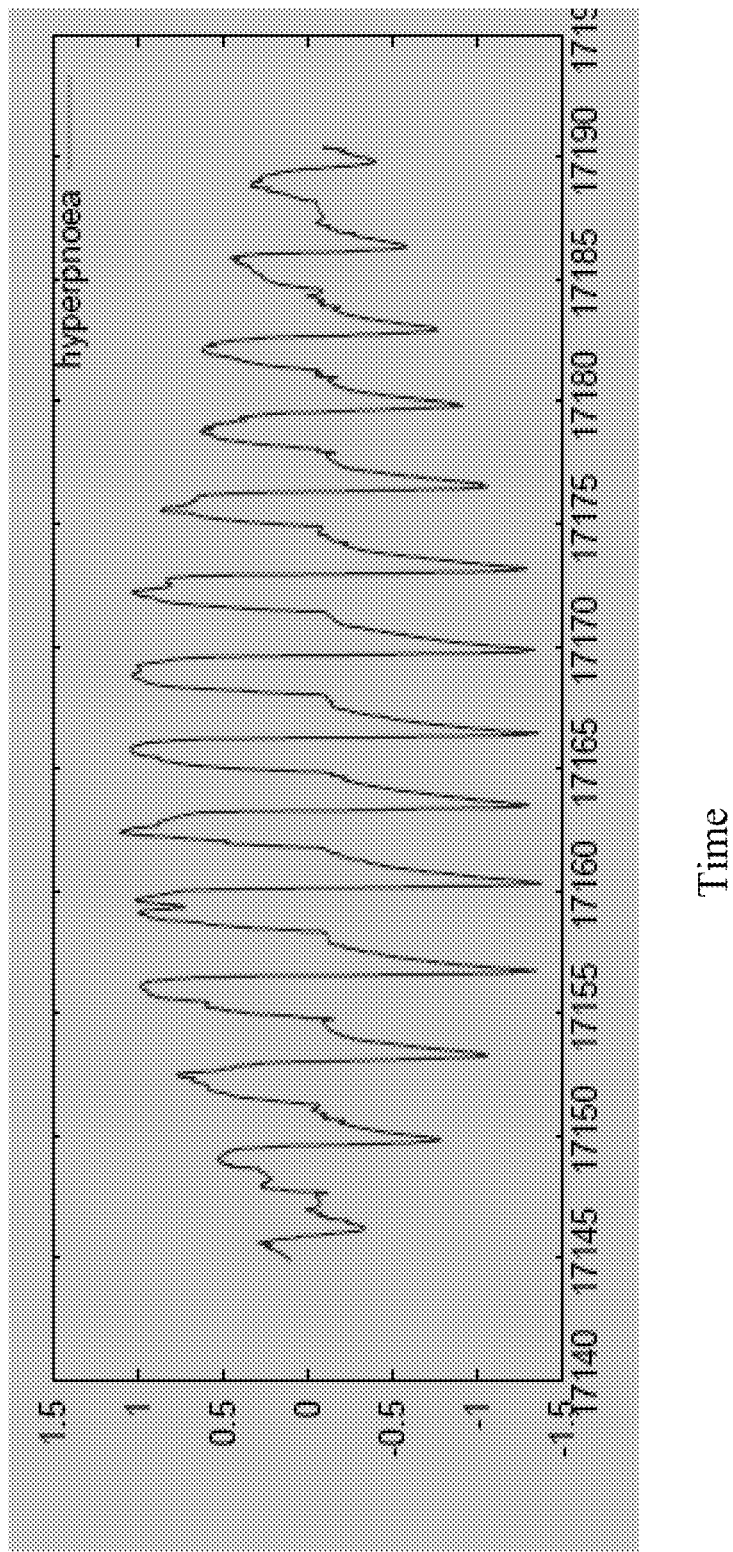
FIG. 11 depicts those parts of the flow waveform that correspond to hyperpnoeas.

All events outside these limits are rejected and not processed. We now have event timings and the ability to extract parts of the flow waveform for further analysis. For example, we can iterate over all the events and select out those parts of the flow waveform that correspond to hyperpnoeas. FIG. 11 is an example where we have selected out an hyperpnoea from the above sequence and plotted it separately. In all further processing it is the 1 Hz filtered flow signal that is used for feature extraction.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

What is claimed is:

1. A method for diagnosing the presence of sleep disorders comprising the steps of:
    recording a signal representative of respiration from a patient using a logging device which includes a data-acquisition system and a memory,
    processing the respiratory signal either on-board by the recording device or offline using a computer,
    dividing the signal into n epochs of equal length,
    recording events consisting of an hypopnoea followed by an hyperpnoea,
    detecting for each event its beginning and endpoints,
    calculating event lengths, and
    processing each hyperpnoea to derive shape features;
    wherein the shape features are calculated using singular value decomposition of the hyperpnoea ventilation signal by the steps of extracting the hyperpnoea from the respiratory signal, forming a ventilation signal from the respiratory signal,
    scaling the ventilation signal to give a vector of values,
    calculating shape factors from the product of the pseudoinverse of the matrix and the vector of values; and
    the matrix of orthogonal functions is:

$$M_{Basis} = \begin{pmatrix} \frac{1}{\sqrt{\pi}} \sin\left(\frac{t}{2}\right) \\ \frac{1}{\sqrt{\pi}} \cos\left(\frac{t}{2}\right) \\ \frac{\left(3\pi\sin(t) - 8\cos\left(\frac{t}{2}\right)\right)}{\sqrt{\pi(9\pi^2 - 64)}} \\ \frac{\left(3\pi\cos(t) - 4\sin\left(\frac{t}{2}\right)\right)}{\sqrt{\pi(9\pi^2 - 16)}} \end{pmatrix}$$

where t is the time base over the hyperpnoea from 0 to 2 pi.

2. A method for diagnosing the presence of sleep disorders comprising the steps of:
    recording a signal representative of respiration from a patient using a logging device which includes a data-acquisition system and a memory,
    processing the respiratory signal either on-board by the recording device or off line using a computer,
    dividing the signal into n epochs of equal length,
    recording events consisting of an hypopnoea followed by an a hyperpnoea,
    detecting for each event its beginning and end points,
    calculating event lengths,
    processing each hyperpnoea to derive shape features, and
    deriving a jump feature for each hyperpnoea by the steps of: extracting the hyperpnoea from the respiratory signal, forming a ventilation signal from an absolute value of the respiratory signal, and approximating an envelope of the ventilation signal with a droopy peak-detector.

3. The method for diagnosing the presence of sleep disorders of claim 2, wherein the following droopy peak-detector is used to approximate the envelope of the ventilation signal:

$$e[1] = v[1]$$
$$\text{for } i = 2 \ldots m$$
$$\text{if } v[i] \geq e[i-1]$$
$$e[i] = v[i]$$
$$\text{else}$$
$$e[i] = e[i-1] + \frac{1}{2.5 f_s}(v[i] - e[i-1])$$
$$\text{end}$$

where e[i] is the approximate envelope, $f_s$ is a sampling frequency and v[i] is the ventilation signal, wherein
an envelope is interpolated over a time base to give e[i] a maximum positive difference in the interpolated signal in an interval between the beginning of the envelope and the point at which the envelope attains its maximum value is found, and
the maximum difference by a mean value of the ventilation signal to give a jump feature is scaled.

4. A method for diagnosing the presence of sleep disorders comprising the steps of:
    recording a signal representative of respiration from a patient using a logging device which includes a data-acquisition system and a memory,
    processing the respiratory signal either on-board by the recording device or off-line using a computer,
    dividing the signal into n epochs of equal length, recording events consisting of an hypopnoea followed by an hyperpnoea,
detecting for each event its beginning and end points,
calculating event lengths,
processing each hyperpnoea to derive shape features, and
calculating an additional feature from the entire epoch signal from a spectrogram of the epoch signal by:
calculating a mean of the respiratory signal and subtracting said mean from the respiratory signal,
chopping the subtracted signal into n slices,
windowing each slice using a Hanning window,
applying a Fourier transform to each windowed slice yielding a complex vector result for each slice,
determining an absolute value of each complex result so as to yield a real valued vector per slice,
averaging said real valued vectors to yield one vector,
taking a natural log of a subsequent vector,
extracting values in a frequency range of 0 Hz to 0.075 Hz to form a sub-vector,
de-trending the sub-vector and determining its mean, and
calculating the feature as a maximum minus the mean of said de-trended sub-vector.

* * * * *